United States Patent
Kashiwaya (10) Patent No.: US 6,652,905 B2
(45) Date of Patent: Nov. 25, 2003

(54) PIEZOELECTRIC ELEMENT AND PROCESS FOR PRODUCTION THEREOF

(75) Inventor: Toshikatsu Kashiwaya, Inazawa (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 10/354,647

(22) Filed: Jan. 30, 2003

(65) Prior Publication Data

US 2003/0170381 A1 Sep. 11, 2003

Related U.S. Application Data

(62) Division of application No. 09/953,674, filed on Sep. 17, 2001, now Pat. No. 6,565,997.

(30) Foreign Application Priority Data

Sep. 20, 2000 (JP) ......................... 2000-286115

(51) Int. Cl.⁷ ............................. B05D 5/12; H04R 17/00
(52) U.S. Cl. ................. 427/100; 427/383.5; 427/419.2; 427/419.3; 29/25.35
(58) Field of Search .............................. 427/100, 383.5, 427/419.2, 419.3; 29/25.35

(56) References Cited

U.S. PATENT DOCUMENTS

| | | | |
|---|---|---|---|
| 2,906,710 A | 9/1959 | Kulscar et al. | |
| 4,749,668 A * | 6/1988 | Fujino et al. | 501/134 |
| 5,006,956 A * | 4/1991 | Kawakita et al. | 361/321.5 |
| 5,059,566 A * | 10/1991 | Kanai et al. | 501/138 |
| 5,093,757 A * | 3/1992 | Kawakita et al. | 361/321.5 |
| 5,275,988 A * | 1/1994 | Mori et al. | 501/136 |
| 5,376,857 A | 12/1994 | Takeuchi et al. | |
| 5,500,142 A | 3/1996 | Ushida et al. | |
| 5,900,274 A | 5/1999 | Chatterjee et al. | |
| 6,154,239 A | 11/2000 | Chatterjee et al. | |
| 6,329,656 B1 * | 12/2001 | Whatmore | 250/338.2 |

FOREIGN PATENT DOCUMENTS

| | | |
|---|---|---|
| JP | 42-20029 | 10/1967 |
| JP | 50-3519 | 2/1975 |
| JP | 60102779 A | 6/1985 |
| JP | 07315926 A | 12/1995 |
| JP | 157018 * | 6/1997 |
| JP | 11029357 A | 2/1999 |

OTHER PUBLICATIONS

Ouchi, Hiromu, et al. *Piezoelectric Properties of $Pb(Mg_{1/3}Nb_{2/3})O_3$ – $PbTiO_3$ – $PbZrO_3$ Ceramics Modified with Certain Additives*, Journal of the American Ceramic Society, Nov. 21, 1966, vol. 49, No. 11, 577–582.

* cited by examiner

Primary Examiner—Brian K. Talbot
(74) Attorney, Agent, or Firm—Burr & Brown (57) ABSTRACT

A piezoelectric element includes a ceramic substrate, a piezoelectric ceramic composition composed mainly of a $PbMg_{1/3}Nb_{2/3}O_3$—$PbZrO_3$—$PbTiO_3$ ternary system solid solution composition containing 0.05 to 10.0% by weight NiO, based on the ceramic composition. Electrodes are electrically connected to the piezoelectric. The piezoelectric is solidly attached to the ceramic substrate directly or via part of or all of the electrodes. The piezoelectric ceramic composition is represented by the following general formula:

$$Pb_x(Mg_{y/3}Nb_{2/3})_aTi_bZr_cO_3,$$

wherein $0.95 \leq x \leq 1.05$; $0.8 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100, 0.475, 0.425) and (0.375, 0.425, 0.200), and a+b+c=1.000. This piezoelectric element has very high piezoelectric properties, is superior in vibration transmittability between ceramic substrate and piezoelectric, and can provide an actuator or sensor of small size and high integration.

2 Claims, 5 Drawing Sheets

PIEZOELECTRIC ELEMENT AND PROCESS FOR PRODUCTION THEREOF

CROSS REFERENCE TO RELATED APPLICATIONS

This application is a division of U.S. application Ser. No. 09/953,674, filed Sep. 17, 2001, now U.S. Pat. No. 6,565,997 B2 the entirety of which is incorporated herein by reference.

BACKGROUND OF THE INVENTION AND RELATED ART STATEMENT

The present invention relates to a piezoelectric element. More particularly, the present invention relates to a piezoelectric element which has very high piezoelectric properties, which is superior in vibration transmittability between ceramic substrate and piezoelectric, and which can provide an actuator or sensor of small size and high integration; as well as to a process for producing such a piezoelectric element.

In recent years, piezoelectric elements have been used in ink jet printer heads, speakers, microphones, etc. As the piezoelectric elements, there are known those comprising a ceramic substrate, a piezoelectric made of a ceramic composition, formed on the substrate, and electrodes electrically connected to the piezoelectric. As to the ceramic composition constituting the piezoelectric, various improved compositions have been disclosed.

For example, a $PbTiO_3$—$PbZrO_3$ binary system solid solution composition, a $Pb(Mg_{1/3}Nb_{2/3})O_3$—$PbTiO_3$—$PbZrO_3$ ternary system solid solution composition and a composition wherein part of Pb and Mg in either of the above composition is replaced by Ni, Nb, Mn, etc., were disclosed [JP-B-50-3519, JP-B-60-102779, Journal of The American Ceramic Society; 49[11] 577 (1966)]. These compositions are improved in piezoelectric properties (e.g. piezoelectric d constant) which are the most important factor determining the piezoelectric element properties. By using a piezoelectric made of such an improved ceramic composition, a piezoelectric element having superior piezoelectric properties is expectable.

When a piezoelectric element is produced actually by coating a piezoelectric material made of the above ceramic composition, on a ceramic substrate and then heat-treating the coated piezoelectric material, however, the obtained piezoelectric has a low density; therefore, there have been pointed out such problems that the piezoelectric element has a low flexural displacement or, when a voltage is applied thereto, it causes dielectric breakdown at the low density area.

Hence, there has been used a piezoelectric element produced by heat-treating beforehand a piezoelectric material made of the above ceramic composition and then attaching this piezoelectric onto a ceramic substrate (JP-A-11-29357).

In this piezoelectric element, attention was paid to a fact that use of a ceramic substrate impairs the densification of a piezoelectric formed on the ceramic substrate. Thus, the piezoelectric element was accordingly improved in piezoelectric properties by means of obtaining a dense piezoelectric by heat-treating a piezoelectric material made of a ceramic composition before attachment to a substrate.

In this piezoelectric element, however, it is necessary to use an inorganic or organic adhesive at the time of attaching the piezoelectric onto the ceramic substrate. Therefore, there have been such problems that the adhesive impairs the vibration transmittability between the ceramic substrate and the piezoelectric or the adhesive components infiltrate into the piezoelectric or the ceramic substrate, deteriorating their properties.

Further, the above-mentioned conventional ceramic compositions have had no sufficiently satisfactory piezoelectric properties.

SUMMARY OF THE INVENTION

The present invention has been completed in view of the above-mentioned problems and aims at providing a piezoelectric element which has very high piezoelectric properties, which is superior in vibration transmittability between ceramic substrate and piezoelectric, and which can provide an actuator or sensor of small size and high integration, and a process for producing such a piezoelectric element.

The present inventor made a study in order to solve the above-mentioned problems. As a result, the present inventor found out that when there is used a piezoelectric material composed mainly of a $PbMg_{1/3}Nb_{2/3}O_3$—$PbZrO_3$—$PbTiO_3$ ternary system solid solution composition of particular formulation and containing NiO in a particular proportion, the piezoelectric material can be densified even when it is coated on a ceramic substrate and then heat-treated, whereby can be obtained a piezoelectric having very high piezoelectric properties. The present invention has been completed based on the above finding.

According to the present invention, there is provided a piezoelectric element including a ceramic substrate, and a piezoelectric(s) made of a ceramic composition composed mainly of a $PbMg_{1/3}Nb_{2/3}O_3$—$PbZrO_3$—$PbTiO_3$ ternary system solid solution composition, the chemical formula of which is discussed below. The piezoelectric(s) contain 0.05 to 10.0% by weight, based on the ceramic composition, of NiO. Electrodes are electrically connected to the piezoelectric, which is solidly attached to the ceramic substrate directly or via part or all of the electrodes.

The piezoelectric ceramic composition is represented by the following general formula:

$$Pb_x(Mg_{y/3}Nb_{2/3})_aTi_bZr_cO_3,$$

wherein $0.95 \leq x \leq 1.05$; $0.8 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100, 0.475, 0.425) and (0.375, 0.425, 0.200), and a+b+c 1.000.

In the piezoelectric element of the present invention, it is preferred that NiO is dispersed in the ceramic composition in such a concentration gradient that the concentration of NiO becomes higher from the interface between the piezoelectric and the ceramic substrate or the electrode(s) towards the thickness direction of the piezoelectric.

Pb in the ceramic composition may be replaced by at least one kind of element selected from the group consisting of Sr, Ca and Ba, in an amount of 2 to 10 mole %. Pb in the ceramic composition may also be replaced by La in an amount of 0.2 to 1.0 mole %.

The ceramic substrate preferably has a thickness of 3 μm to 1 μm, and the piezoelectric preferably has a thickness of 1 to 300 μm. The ratio of the thickness of the ceramic substrate to the thickness of the piezoelectric (the thickness of the ceramic substrate/the thickness of the piezoelectric) is preferably 0.1 to 30.

According to the present invention, there is also provided a process for producing a piezoelectric element, which includes the steps:

coating, on a ceramic substrate or on an electrode(s) formed on a ceramic substrate, a piezoelectric material made of a ceramic composition composed mainly of a $PbMg_{1/3}Nb_{2/3}O_3$—$PbZrO_3$—$PbTiO_3$ ternary system solid solution composition, the chemical formula of which is discussed below. The piezoelectric material contains 0.05 to 10.0% by weight, based on the ceramic composition, of NiO; and heat-treating the coated piezoelectric material in the co-presence of an atmosphere-controlling material having a formulation of the ceramic NiO content as the ceramic composition or a formulation of higher NiO content than the ceramic composition.

The piezoelectric ceramic composition is represented by the following general formula:

$Pb_x(Mg_{y/3}Nb_{2/3})_aTi_bZr_cO_3$, wherein $0.95 \leq x \leq 1.05$; $0.8 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100, 0.475, 0.425) and (0.375, 0.425, 0.200), and a+b+c=1.000.

According to the present invention, there is also provided a process for producing a piezoelectric element, which includes the steps of:

preparing a plurality of different piezoelectric materials each made of a ceramic composition composed mainly of a $PbMg_{1/3}Nb_{2/3}O_3$—$PbZrO_3$—$PbTiO_3$ ternary system solid solution composition, the chemical formula of which is discussed below, and having a different NiO content;

coating in order of the low NiO content these piezoelectric materials on a ceramic substrate or on an electrode(s) formed on a ceramic substrate; and heat-treating the coated piezoelectric materials.

The piezoelectric ceramic composition is represented by the following general formula:

$Pb_x(Mg_{y/3}Nb_{2/3})_aTi_bZr_cO_3$, wherein $0.95 \leq x \leq 1.05$; $0.8 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100, 0.475, 0.425) and (0.375, 0.425, 0.200), and a+b+c=1.000.

The piezoelectric element according to the present invention can be used in capacitors or various sensors, as a dense and small dielectric element or pyroelectric element.

BRIEF DESCRIPTION OF THE DRAWINGS

FIGS. 1(a) and (b) schematically show an embodiment of the piezoelectric element of the present invention.

FIGS. 2(a) and (b) schematically show another embodiment of the piezoelectric element of the present invention.

FIGS. 3(a) and (b) schematically show still another embodiment of the piezoelectric element of the present invention.

FIGS. 4(a) and (b) schematically show still another embodiment of the piezoelectric element of the present invention.

FIGS. 5(a) and (b) schematically show still another embodiment of the piezoelectric element of the present invention.

DETAILED DESCRIPTION OF THE INVENTION

The present invention is described in detail below with reference to the accompanying drawings.

1. Piezoelectric Element

Figure 1A:
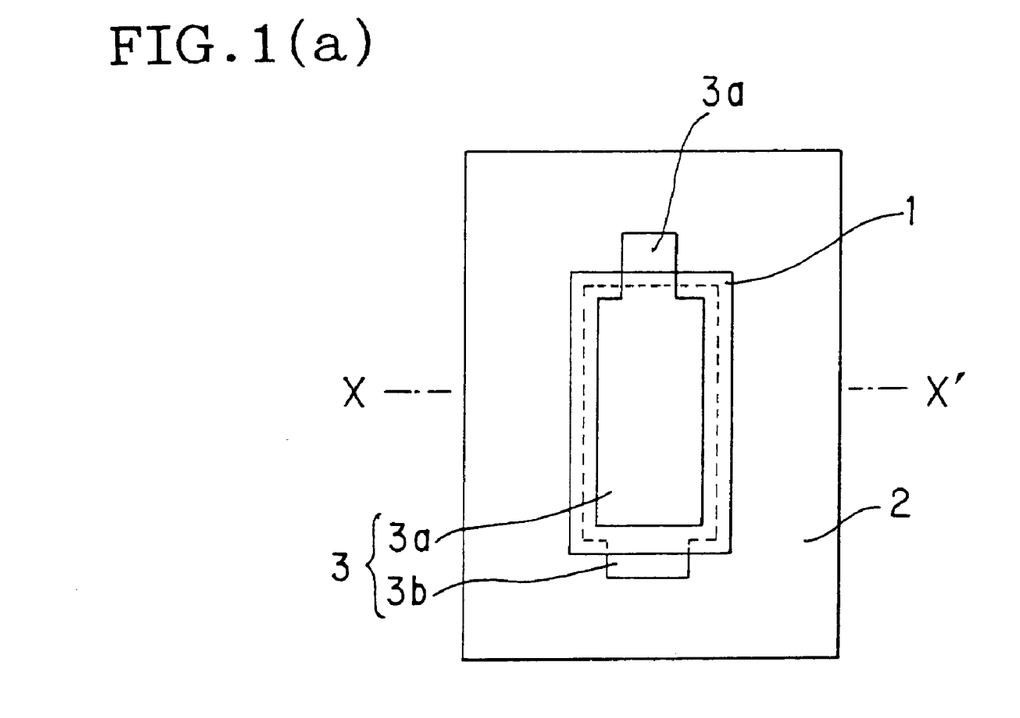
FIG. 1(a) is a plan view and FIG. 1(b) is a sectional view taken along the X–X' line of FIG. 1(a).
Figure 1B:
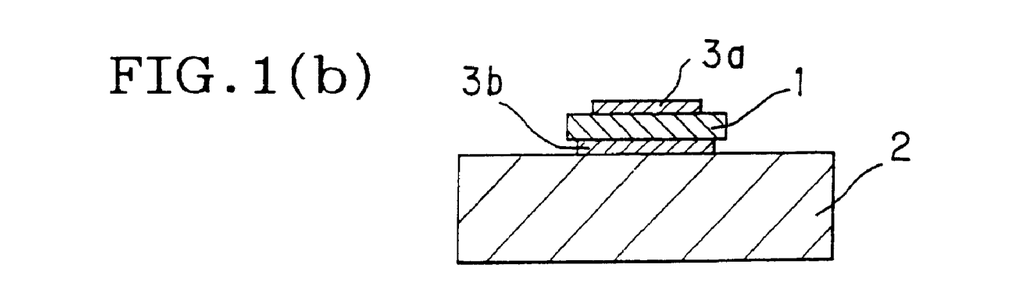

As shown in FIGS. 1(a) and (b), the piezoelectric element of the present invention includes: a ceramic substrate 2, a piezoelectric 1 composed mainly of a particular ceramic composition, and electrodes 3 (3a and 3b) electrically connected to the piezoelectric 1. The piezoelectric 1 is solidly attached to the ceramic substrate 2 directly or via part of or all of the electrodes 3.

The present piezoelectric element is described specifically below.

The ceramic substrate 2 used in the present piezoelectric element is preferably made of a material containing at least one kind selected from the group consisting of stabilized zirconium oxide, aluminum oxide, magnesium oxide, mullite, aluminum nitride, silicon nitride and glass, for the heat resistance, chemical stability and insulating property.

Of these, particularly preferred is a material containing stabilized zirconium oxide, for the high mechanical strength and superior toughness.

The ceramic substrate 2 has a thickness of preferably 3 µm to 1 mm, more preferably 5 to 500 µm, particularly preferably 7 to 200 µm.

When the thickness is less than 3 µm, the piezoelectric element may have a low mechanical strength; when the thickness is more than 1 mm, the rigidity of the ceramic substrate 2 relative to the shrinkage stress of the piezoelectric 1 is large when a voltage is applied to the piezoelectric element, and the piezoelectric element may show a small flexural displacement.

Figure 2A:
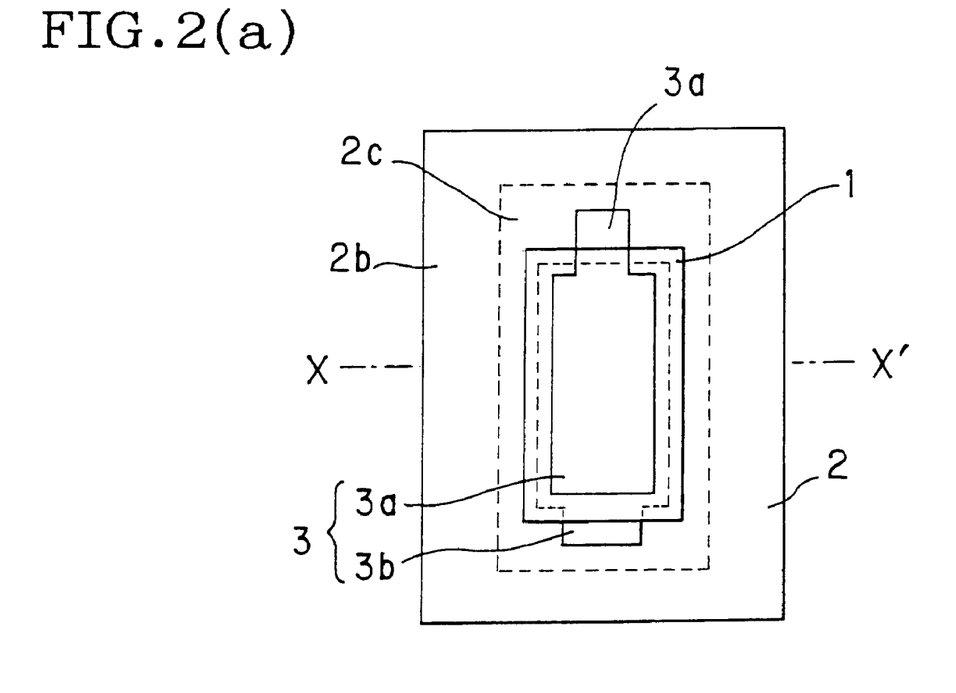
FIG. 2(a) is a plan view and FIG. 2(b) is a sectional view taken along the X–X' line of FIG. 2(a).
Figure 2B:
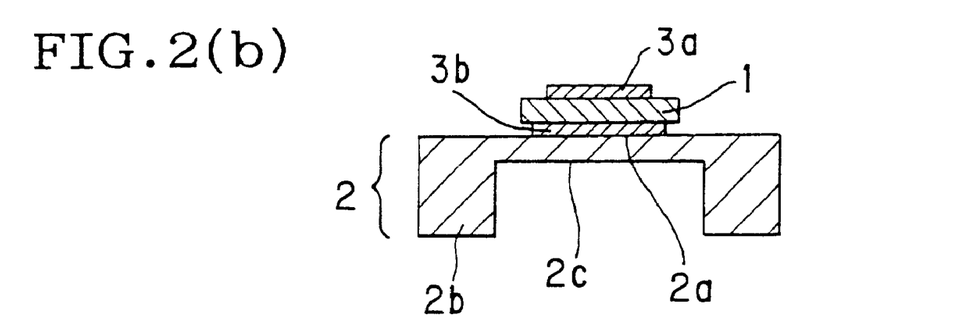

The ceramic substrate 2 may be produced so as to have, as shown in FIGS. 2(a) and (b), a thin portion 2c roughly corresponding to an interface 2a between piezoelectric 1 or electrode 3b and ceramic substrate 2, and having the above-mentioned thickness. The ceramic substrate has a thick portion 2b roughly corresponding to the surface area of ceramic substrate other than the interface 2a, and having a larger thickness than the thin portion 2c.

Thereby, the piezoelectric element obtained can show a larger flexural displacement and a higher mechanical strength.

Figure 3A:
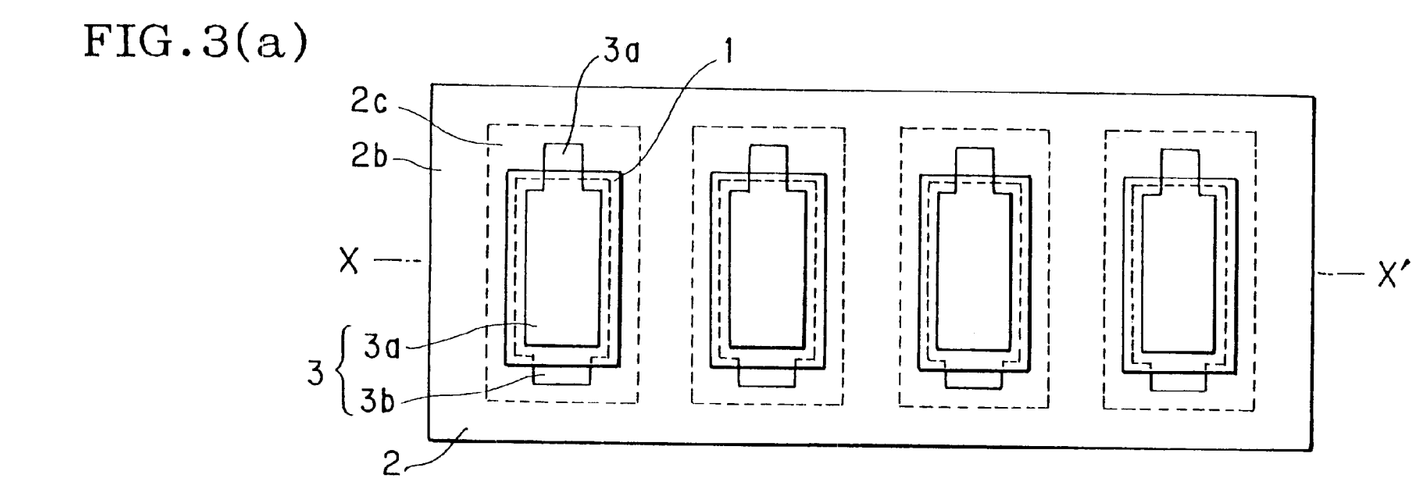
FIG. 3(a) is a plan view and FIG. 3(b) is a sectional view taken along the X–X' line of FIG. 3(a).
Figure 3B:
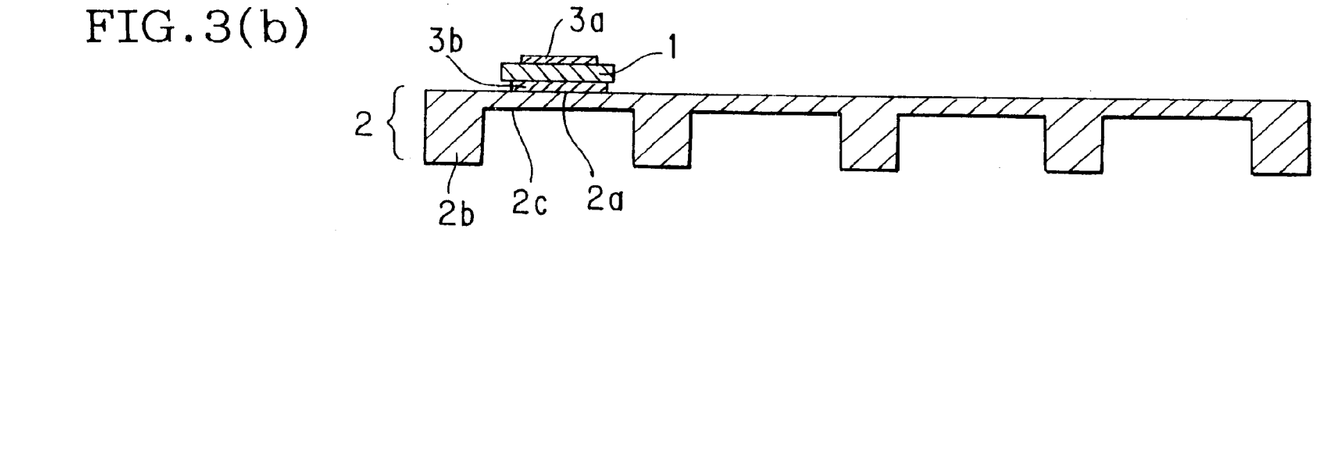

It is also possible that a plurality of units each consisting of a piezoelectric and electrodes are provided on a single large ceramic substrate 2, as shown in FIGS. 3(a) and (b).

There is no particular restriction as to the surface shape of the ceramic substrate 2. As the surface shape, there can be mentioned, for example, a rectangle, a square, a triangle, an ellipse, a true circle, an edge-rounded square, an edge-rounded rectangle, a capsule and combinations thereof.

The piezoelectric 1 used in the present piezoelectric element is made of a ceramic composition composed mainly of a $PbMg_{1/3}Nb_{2/3}O_3$—$PbZrO_3$—$PbTiO_3$ ternary system solid solution composition represented by the general chemical formula shown below, and containing NiO in a particular proportion.

The piezoelectric ceramic composition is represented by:

$$Pb_x(Mg_{y/3}Nb_{2/3})_a Ti_b Zr_c O_3,$$

wherein $0.95 \leq x \leq 1.05$; $08 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100,0.475,0.425) and (0.375,0.425,0.200), and a+b+c=1.000.

Thereby, the ceramic composition can have improved piezoelectric properties and the piezoelectric 1 can have a high density, making it possible to obtain a piezoelectric element showing an improved flexural displacement.

The reason why, in the general formula shown above, that a, b and c fall in the above-mentioned particular range, is that, if a, b and c are outside of the range, the piezoelectric element shows a small flexural displacement.

The NiO content in the ceramic composition is 0.05 to 10.0% by weight, preferably 0.50 to 8.0% by weight, more preferably 1.0 to 6.0% by weight.

When the NiO content is less than 0.05% by weight, the densification of the piezoelectric is insufficient and the piezoelectric element obtained therewith shows a small flexural displacement. When the NiO content is more than 10.0% by weight, the piezoelectric has a higher reactivity with the ceramic substrate 2 and the piezoelectric element obtained therewith shows a small flexural displacement.

NiO is dispersed in the ceramic composition preferably uniformly and more preferably in such a concentration gradient that the concentration of NiO becomes higher from the interface 2a between the piezoelectric 1 and the ceramic substrate 2 or the electrode(s) 3 towards the thickness direction of the piezoelectric 1.

Thereby, the piezoelectric 1 can have a higher density even when it is solidly attached to the ceramic substrate 2 directly or via an electrode(s) 3.

In order to allow the ceramic composition per se to have large piezoelectric properties, it is preferred to replace the Pb in the ceramic composition by at least one kind of element selected from the group consisting of Sr, Ca, Ba and La.

When the Pb in the ceramic composition is replaced by at least one kind of element selected from the group consisting of Sr, Ca and Ba, the Pb is replaced preferably in an amount of 2 to 10 mole %, more preferably 4 to 8 mole %.

When the Pb is replaced by less than 2 mole %, the resulting piezoelectric element may show a small flexural displacement; when the Pb is replaced by more than 10 mole %, the resulting piezoelectric element has a low Curie point and its flexural displacement may change largely with temperature.

When the Pb in the ceramic composition is replaced by La, the Pb is replaced preferably in an amount of 0.2 to 1.0 mole %, more preferably 0.4 to 0.9 mole %.

When the Pb is replaced by less than 0.2 mole %, the resulting piezoelectric element may show a small flexural displacement; when the Pb is replaced by more than 1.0 mole %, the resulting piezoelectric element has a low Curie point and its flexural displacement may change largely with temperature.

The piezoelectric 1 preferably has an average grain diameter of 1 to 20 µm, more preferably 2 to 10 µm.

When the average grain diameter is less than 1 µm, the domain in the piezoelectric 1 does not develop sufficiently, which may result in a small flexural displacement. When the average grain diameter is more than 20 µm, the domain in the piezoelectric 1 is large but does not move easily, which may result in a small flexural displacement.

The piezoelectric 1 contains a phase(s) other than perovskite phase preferably by 20% by volume or less, more preferably by 10% by volume or less.

When the piezoelectric 1 contains a phase(s) other than perovskite phase by more than 20% by volume, the resulting piezoelectric element may show a small flexural displacement.

The piezoelectric 1 has a porosity of preferably 10% by volume or less, more preferably 5% by volume or less.

When the porosity is more than 10% by volume, the resulting piezoelectric element shows a small flexural displacement and may have small mechanical strengths.

The piezoelectric 1 has a thickness of preferably 1 to 300 µm, more preferably 3 to 100 µm, particularly preferably 5 to 30 µm.

When the thickness is less than 1 µm, the piezoelectric 1 made of a particular ceramic composition us ed in the present invention is difficult to densify sufficiently and the resulting piezoelectric element may show a small flexural displacement. When the thickness is more than 300 µm, the stress to the ceramic substrate 2 becomes relatively too large; in order to prevent the substrate fracture, the ceramic substrate 2 needs to have a large thickness, making it difficult to produce a small piezoelectric element required in practical application.

The ratio of the thickness of the ceramic substrate 2 to the thickness of the piezoelectric 1 (the thickness of the ceramic substrate/the thickness of the piezoelectric) is preferably 0.1 to 30, more preferably 0.3 to 10, particularly preferably 0.5 to 5.

When the ratio is less than 0.1, the resulting piezoelectric element may have small mechanical strengths. When the ratio is more than 30, the resulting piezoelectric element may show a small flexural displacement.

Figure 4A:
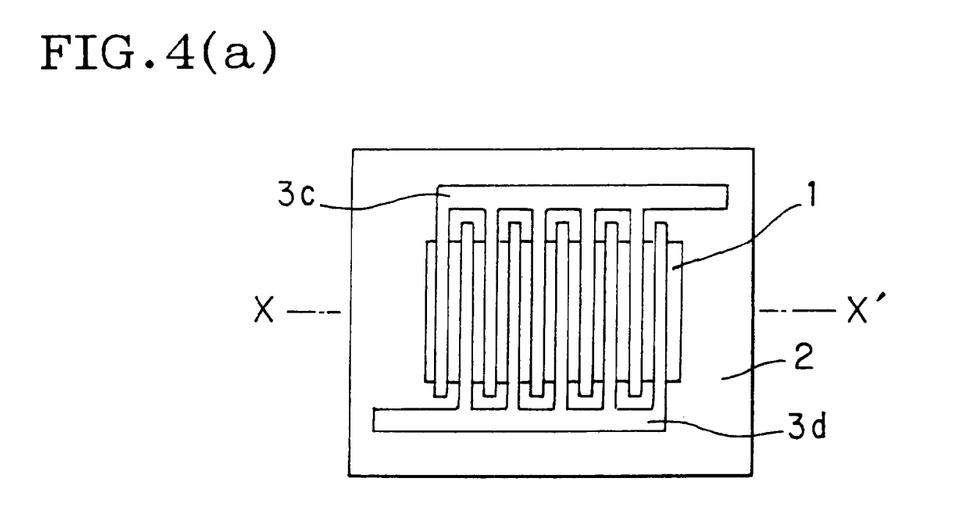
FIG. 4(a) is a plan view and FIG. 4(b) is a sectional view taken along the X–X' line of FIG. 4(a).
Figure 4B:
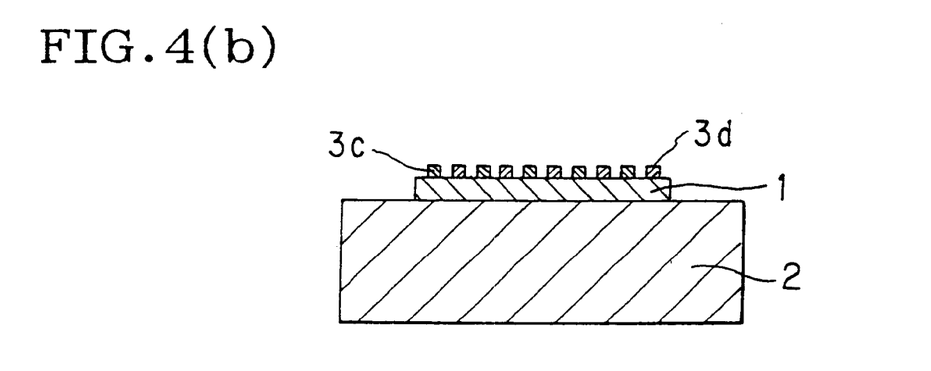
Figures 5A, 5B:
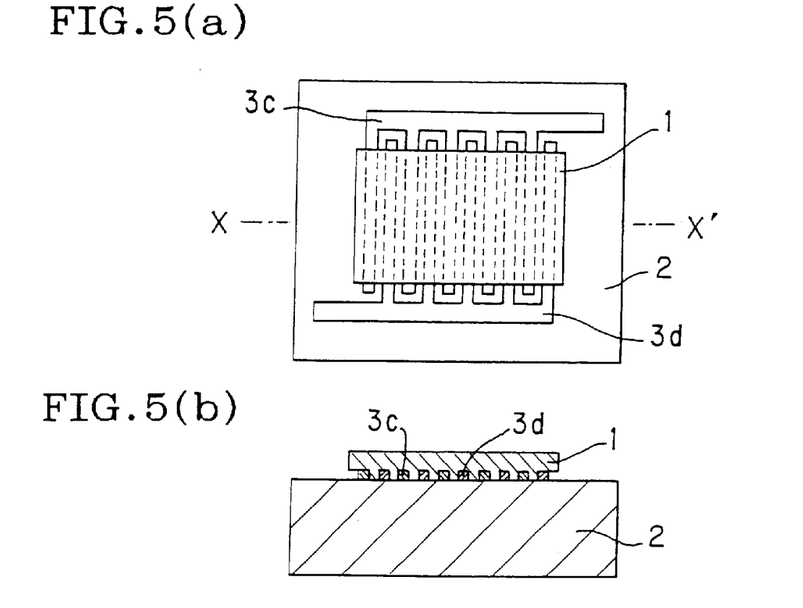
FIG. 5(a) is a plan view and FIG. 5(b) is a sectional view taken along the X–X' line of FIG. 5(a).

There is no particular restriction as to the electrodes 3 used in the piezoelectric element of the present invention, except that they are electrically connected to the piezoelectric 1. The electrodes 3 may be, for example, a pair of comb-shaped electrodes 3c and 3d formed on a piezoelectric 1 attached solidly to a ceramic substrate 2, as shown in FIGS. 4(a) and (b); or, may be a pair of comb-shaped electrodes 3c and 3d attached solidly to a ceramic substrate 2 (in this case, a piezoelectric 1 is solidly attached onto the electrodes 3c and 3d), as shown in FIGS. 5(a) and (b).

Figure 6:
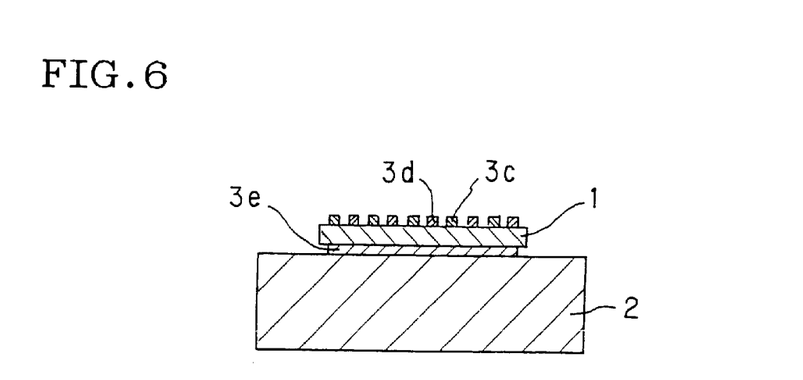
FIG. 6 is a sectional view schematically showing still another embodiment of the piezoelectric element of the present invention.
Figure 7:
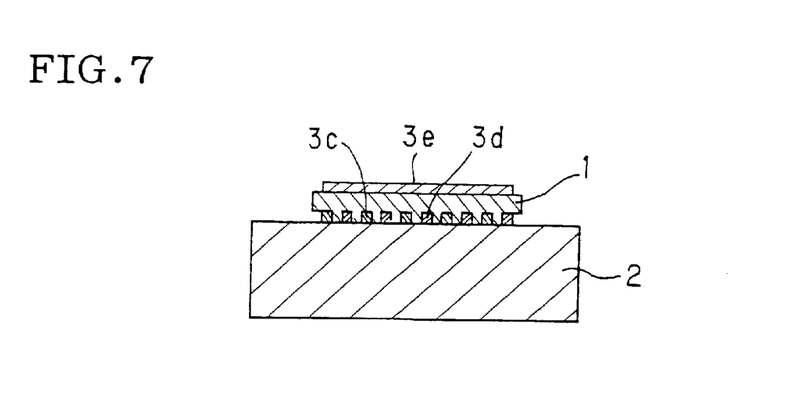
FIG. 7 is a sectional view schematically showing still another embodiment of the piezoelectric element of the present invention.

Alternatively, it is possible that, as shown in FIG. 6, a common electrode 3e is solidly attached onto a ceramic substrate 2, a piezoelectric 1 is solidly attached onto the common electrode 3e, and a pair of comb-shaped electrodes 3c and 3d are formed on the piezoelectric 1. It is also possible that, as shown in FIG. 7, a pair of comb-shaped electrodes 3c and 3d are solidly attached onto a ceramic substrate 2, a piezoelectric 1 is solidly attached onto the comb-shaped electrodes 3c and 3d, and a common electrode 3e is formed on the piezoelectric 1.

As the material for the electrodes 3, there can be mentioned at least one kind of material selected from the group consisting of platinum, palladium, rhodium, silver and alloys thereof.

Of these materials, platinum or an alloy composed mainly of platinum is preferred because they show high heat resistance during the heat-treatment of piezoelectric 1.

The thickness of electrodes 3 are preferably 15 µm or less, more preferably 5 µm or less.

When the thickness is more than 15 μm, the electrodes 3 act as a relaxing layer, which may result in a small flexural displacement.

The electrodes 3 are heat-treated as necessary and integrated with the ceramic substrate 2.

In the piezoelectric element of the present invention, the above-mentioned piezoelectric 1 is solidly attached to the above-mentioned ceramic substrate 2 directly or via part or all of the above-mentioned electrodes 3.

Thereby, it is possible to prevent the reduction in vibration transmittability between ceramic substrate 2 and piezoelectric 1, caused by the interposition of adhesive or the like, and the deterioration of properties of piezoelectric 1 and ceramic substrate 2, caused by the infiltration of adhesive components or the like and the resulting reduction in flexural displacement.

Herein, "be solidly attached" refers to that the piezoelectric 1 is tightly integrated with the ceramic substrate 2 directly or via part or all of the electrodes 3, owing to a solid-state reaction between the ceramic substrate 2 and the piezoelectric 1 or the electrode(s) 3, without using any adhesive of organic or inorganic type.

The piezoelectric element of the present invention can be produced by the first or second process described below.

2. First Process

The first process of the present invention comprises coating a piezoelectric material composed mainly of a particularly ceramic composition, on a ceramic substrate or an electrode(s) formed on a ceramic substrate, and heat-treating the coated ceramic material in the co-presence of an atmosphere-controlling material having a particular formulation.

Specific description is made below.

In the first process of the present invention, first, a piezoelectric material made of a particular ceramic composition is coated on a ceramic substrate or an electrode(s) formed on a ceramic substrate.

The ceramic substrate used in the first process is the same as described with respect to the piezoelectric element of the present invention.

The piezoelectric material used in the first process is made of a ceramic composition composed mainly of a $PbMg_{1/3}Nb_{2/3}O_3$—$PbZrO_3$—$PbTiO_3$ ternary system solid solution composition, represented by the general formula shown below, and containing NiO in a particular proportion.

The ceramic composition is represented by:

$Pb_x(Mg_{y/3}Nb2/3)_aTi_bZr_cO_3,$ wherein $0.95 \leq x \leq 1.05$; $0.8 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100, 0.475, 0.425) and (0.375, 0.425, 0.200), and a+b+c=1.000.

Thereby, the ceramic composition can have improved piezoelectric properties and the piezoelectric can have a high density, making it possible to obtain a piezoelectric element having high piezoelectric properties.

The reason why, in the general formula shown above, that a, b and c fall in the above-mentioned particular range, is that, if a, b and c are outside of the range, the piezoelectric element shows a small flexural displacement.

The NiO content in the ceramic composition is 0.05 to 10.0% by weight, preferably 0.50 to 8.0% by weight, more preferably 1.0 to 6.0% by weight.

When the NiO content is less than 0.05% by weight, the densification of the piezoelectric is insufficient and the piezoelectric element obtained therewith shows a small flexural displacement. When the NiO content is more than 10.0% by weight, the piezoelectric has a higher reactivity with the ceramic substrate and the piezoelectric element obtained therewith shows a small flexural displacement as well.

As the raw materials for the composition represented by the general formula shown above, there can be mentioned, for example, simple substances (elements) each consisting of Pb, Ba, Ca, Sr, La, Mg, Nb, Zr or Ti; oxides of these elements (e.g. PbO, $Pb_3O_4$, $La_2O_3$, MgO, $Nb_2O_5$, $TiO_2$ and $ZrO_2$); carbonates of these elements (e.g. $BaCO_3$, $SrCO_3$, $MgCO_3$ and $CaCO_3$); and compounds containing a plurality of these elements (e.g. $MgNb_2O$).

These raw materials for piezoelectric material can be used singly or in combination of two or more kinds per each elements.

There is no particular restriction as to the method for preparing the piezoelectric material. However, the piezoelectric material can be prepared by following method, for example.

First, the above-mentioned raw materials are mixed so that the contents of elements (Pb, Ba, Ca, Sr, La, Mg, Nb, Zr and Ti) in resulting mixture become as desired relative to the general formula shown above; the mixture is mixed with NiO in the above-mentioned given proportions; the resulting mixed raw material is calcinated at 750 to 1,300° C. to obtain a desired ceramic composition.

Lastly, the calcinated piezoelectric material is ground to obtain a piezoelectric material having desired particle diameters.

The piezoelectric material may be prepared by other method, for example, an alkoxide method or a co-precipitation method.

There is no particular restriction as to the method for coating the piezoelectric material. However, as the method, there can be mentioned, for example, an ion beam method, sputtering, vacuum deposition, PVD, ion plating, CVD, plating, screen printing, spraying and dipping.

Of these, sputtering and screen printing are preferred because they enable simple and continuous coating in a shape and thickness of high accuracy.

In the first process, a piezoelectric material can be coated directly on a ceramic substrate. Alternatively, an electrode(s) can be formed on a ceramic substrate and a piezoelectric material can be coated on the electrode(s).

As the method for forming the electrode(s), there can be mentioned, for example, an ion beam method, sputtering, vacuum deposition, PVD, ion plating, CVD, plating, screen printing, spraying and dipping.

Of these, sputtering and screen printing are preferred in view of the bondability between ceramic substrate or piezoelectric.

As the material used for forming the electrode(s), there can be mentioned at least one kind of material selected from the group consisting of platinum, palladium, rhodium, silver and alloys thereof.

Of these materials, platinum or an alloy composed mainly of platinum is preferred because they show high heat resistance during the heat-treatment of piezoelectric.

The thickness of electrode(s) formed is(are) preferably 15 μm or less, more preferably 5 μm or less.

When the thickness is more than 15 μm, the electrode(s) act as a relaxing layer and the piezoelectric element may show a small flexural displacement.

The electrode(s) is (are) heat-treated as necessary and integrated with the ceramic substrate.

In the first process of the present invention, then, the piezoelectric material coated on the ceramic substrate is heat-treated in the co-presence of an atmosphere-controlling material having a formulation of the same NiO content as the ceramic composition or a formulation of higher NiO content than the ceramic composition.

Thereby, it becomes possible to prevent the vaporization of NiO present in the ceramic composition constituting the piezoelectric material and obtain a piezoelectric wherein NiO is dispersed uniformly or in a such a concentration gradient that the concentration of NiO becomes higher from the interface between the piezoelectric and the ceramic substrate or the electrode(s) towards the thickness direction of the piezoelectric; and it becomes also possible to solidly attach,the piezoelectric to the ceramic substrate.

Specifically, by making the NiO content in the atmosphere-controlling material the same as the NiO content in the ceramic composition constituting the piezoelectric material, it becomes possible to obtain a piezoelectric wherein NiO is dispersed uniformly; and by making the NiO content in the atmosphere-controlling material higher than the NiO content in-the ceramic composition constituting the piezoelectric material, it becomes possible to obtain a piezoelectric wherein NiO is dispersed in a such a concentration gradient that the concentration of NiO becomes higher from the interface between the piezoelectric and the ceramic substrate or the electrode(s) towards the thickness direction of the piezoelectric. Also, by controlling the NiO content in the atmosphere-controlling material, it becomes possible to control the extent of the NiO concentration gradient in the piezoelectric obtained.

There is no particular restriction as to the components other than NiO, of the atmosphere-controlling material. However, it is preferred that the kinds and contents of other components in the atmosphere-controlling material are made the same as in the ceramic composition constituting the piezoelectric material, in order to prevent the vaporization of the components (other than NiO).

In the first process, the heat treatment temperature is preferably 1,000 to 1,400° C., more preferably 1,100 to 1,350° C.

When the temperature is less than 1,000° C., the solid attachment of the piezoelectric to the ceramic substrate may be insufficient or the density of the piezoelectric may be insufficient. When the temperature exceeds 1,400° C., the vaporization amount of Pb in the piezoelectric material is large and it may be difficult to obtain a piezoelectric having an intended composition.

The heat treatment may be conducted after formation of electrode(s) or before the formation.

3. Second Process

The second process of the present invention comprises preparing a piezoelectric material made of a particular ceramic composition, coating the piezoelectric material on a ceramic substrate or an electrode(s) formed on a ceramic substrate by a particular method, and heat-treating the coated piezoelectric material.

The second process is described specifically below.

In the second process of the present invention, first, there are prepared a plurality of different piezoelectric materials each made of a ceramic composition composed mainly of a particular composition and containing NiO in a different proportion. The ceramic composition used in preparing the piezoelectric material can be the same ceramic composition as used in the first process, and the preparation of the piezoelectric material can be conducted in the same manner as described in the first process.

Incidentally, the second process is different from the first process in that the former process uses a plurality of different piezoelectric materials each made of a ceramic composition of different NiO content.

In the present second process, then, the plurality of different piezoelectric materials each made of a ceramic composition of different NiO content are coated in order of the low NiO content piezoelectric materials on a ceramic substrate or an electrode(s) formed on a ceramic substrate.

Thereby, it is possible to reliably obtain a piezoelectric wherein NiO is dispersed in such a concentration gradient that the concentration of NiO becomes higher from the interface between the piezoelectric and the ceramic substrate or the electrode(s) towards the thickness direction of the piezoelectric.

There is no particular restriction as to the method for coating the piezoelectric materials, and the piezoelectric materials can be coated in the same manner as in the first process.

In the second process of the present invention, then, the piezoelectric materials coated on the ceramic substrate or the electrode(s) are heat-treated.

In the heat-treatment, the co-presence of an atmosphere-controlling material containing NiO is unnecessary. However, the co-presence of an atmosphere-controlling material containing NiO is preferred because it can control the NiO concentration gradient in the resulting piezoelectric more accurately.

The heat-treatment may be conducted in one time after all of the different piezoelectric materials of different NiO contents have been coated, or may be conducted every time after each piezoelectric material has been coated.

The heat treatment conditions(the temperature, etc.) are the same as in the first process.

The present invention is described specifically below by way of Examples. However, the present invention is in no way restricted to these Examples.

In Examples and Comparative Examples, measurements were conducted as follows.

1. Flexural Displacement

A voltage was applied to electrodes of a piezoelectric element so as to give an electric field of 3 kV/mm. The resulting flexural displacement of the piezoelectric element was measured by a laser displacement tester.

2. Porosity

The piezoelectric of each piezoelectric element obtained in Examples and Comparative Examples was examined by a scanning electron microscope, over a range of 50 $\mu$m of each of the surface, length and width; the areal proportion of pores in each of the three visual fields was determined; and the average of the three areal proportions was calculated and taken as the porosity of the piezoelectric.

EXAMPLE 1

A lower electrode [1.2 mm×0.8 mm×3 $\mu$m (thickness)] composed of platinum was formed, by screen printing, on a $Y_2O_3$-stabilized $ZrO_2$ substrate [the dimension of thin portion: 1.6 mm×1.1 mm×10 $\mu$m (thickness)]. They were subjected to a heat treatment to integrate the lower electrode with the substrate.

Thereon was coated a piezoelectric material [1.3 mm×0.9 mm×13 μm (thickness)] made of a ceramic composition containing 98.5% by weight of $Pb_{1.00}(Mg_{1/3}Nb_{2/3})_{0.20}Ti_{0.43}Zr_{0.37}O_3$ and 1.5% by weight of NiO, followed by a heat-treatment at 1,275° C. for 2 hours in the co-presence of an atmosphere-controlling material having the same composition as the piezoelectric material. The piezoelectric material after heat treatment had a thickness of 10 μm. Then, thereon was formed, by screen printing, an upper electrode [1.2 mm×0.8 mm×0.5 μm (thickness)] composed of gold. The resulting material was heat-treated to produce a piezoelectric element.

The piezoelectric element was measured for flexural displacement, which was very large at 2.20 μm. The composition of the piezoelectric material used and the flexural displacement of the piezoelectric element obtained are shown in Table 1.

EXAMPLE 2 AND COMPARATIVE EXAMPLES 1 AND 2

Piezoelectric elements were produced in the same manner as in Example 1 except that the piezoelectric material used in Example 1 was changed to those shown in Table 1.

The piezoelectric elements were measured for flexural displacement. The piezoelectric element of Example 2 produced using a piezoelectric material having a, b and c falling in the range of the present invention, showed a large flexural displacement of 2.22 μm. In contrast, the piezoelectric elements of Comparative Examples 1 and 2 each using a piezoelectric material having a, b and c deviating from the range of the present invention, showed small flexural displacements of 1.56 μm and 1.38 μm, respectively. The results are shown in Table 1.

REFERENCE EXAMPLES 1 TO 3

Piezoelectric elements were produced in the same manner as in Example 1 except that there were used, as piezoelectric materials, those obtained by mixing 97% by volume, 93% by volume or 85% by volume of a piezoelectric material (containing 98.5% by weight of $Pb_{1.00}(Mg_{1/3}N_{2/3})_{0.20}Ti_{0.43}Zr_{0.37}O_3$ and 1.5% by weight of NiO), with 3% by volume, 7% by volume or 15% by volume of a latex having particle diameters of 8 to 12 μm (this latex was oxidized and gasified by a heat-treatment and, thereby, generated pores at the sites where it had existed before the heat treatment).

In the piezoelectric of Reference Example 3 having a large latex content in the piezoelectric and a porosity of 19%, the flexural displacement was 1.77 μm; in the piezoelectric of Reference Example 2 having a porosity of 10%, the flexural displacement was 2.08 μm; and in the piezoelectric of Reference Example 1 having a porosity of 5%, the flexural displacement was 2.20 μm. Thus, as the porosity became larger, the flexural displacement was smaller. The results are shown in Table 2.

TABLE 2

|  | Latex amount (vol. %) | Porosity (%) | Flexural Displacement (μm) |
| --- | --- | --- | --- |
| Ref. Ex. 1 | 3 | 5 | 2.20 |
| Ref. Ex. 2 | 7 | 10 | 2.08 |
| Ref. Ex. 3 | 15 | 19 | 1.77 |

EXAMPLE 3 AND COMPARATIVE EXAMPLES 3 AND 4

Piezoelectric elements were produced in the same manner as in Example 1 except that there were used piezoelectric materials each having a composition of NiO content shown in Table 3.

The piezoelectric elements were measured for flexural displacement. In the piezoelectric element of Example 3 using a piezoelectric material of 1.5% by weight in NiO content, the porosity was small at 5% and the flexural displacement was large at 2.20 μm.

In contrast, in the piezoelectric element of Comparative Example 3 using a piezoelectric material of small NiO content (0.03% by weight), the porosity was large at 13% and the flexural displacement was small at 1.77 μm; and in the piezoelectric element of Comparative Example 4 using a piezoelectric material of large NiO content (15.0% by weight), the porosity was small at 4% but the flexural displacement was small at 1.41 μm. The results are shown in Table 3.

TABLE 1

Formulation of $PbMg_{1/3}Nb_{2/3}O_3$—$PbZrO_3$—$PbTiO_3$ ternary system solid solution composition

|  | Pb-replacing element | | | | | | | NiO | Flexural |
| --- | --- | --- | --- | --- | --- | --- | --- | --- | --- |
|  | Kind of element | Proportion (mole %) | x | Y | a | b | c | Content (wt. %) | displacement (μm) |
| Example 1 | None | — | 1.00 | 1.00 | 0.200 | 0.430 | 0.370 | 1.5 | 2.20 |
| Example 2 | Ca | 5.0 | 1.00 | 1.00 | 0.375 | 0.375 | 0.250 | 5.0 | 2.22 |
| Comparative Example 1 | None | — | 1.00 | 1.00 | 0.600 | 0.300 | 0.100 | 8.0 | 1.56 |
| Comparative Example 2 | Sr | 10.0 | 1.00 | 1.00 | 0.150 | 0.350 | 0.500 | 0.5 | 1.38 |

TABLE 3

|  | NiO content (wt. %) | Porosity (%) | Flexural Displacement (μm) |
| --- | --- | --- | --- |
| Example 3 | 1.5 | 5 | 2.20 |
| Comp. Ex. 3 | 0.03 | 13 | 1.77 |
| Comp. Ex. 4 | 15.0 | 4 | 1.41 |

EXAMPLE 4

A piezoelectric element was produced in the same manner as in Example 1 except that there was used, as a piezoelectric material, a ceramic composition containing 98.0% by weight of $Pb_{1.00}(Mg_{0.97/3}Nb_{2/3})_{0.20}Ti_{0.43}Zr_{0.37}O_3$ and 2.0% by weight of NiO.

The piezoelectric element was measured for flexural displacement, which was relatively large at 2.11 μm. Further, the dispersion state of NiO in piezoelectric was examined by an EPMA analysis, which indicated that NiO was dispersed uniformly. The results are shown in Table 4.

EXAMPLE 5

A piezoelectric element was produced in the same manner as in Example 1 except that there were used a ceramic composition containing 98.0% by weight of $Pb_{1.00}(Mg_{0.97/3}Nb_{2/3})_{0.20}Ti_{0.43}Zr_{0.37}O_3$ and 2.0% by weight of NiO and, as a atmosphere-controlling material, a ceramic composition containing 90.0% by weight of $Pb_{1.00}(Mg_{0.97/3}Nb_{2/3})_{0.20}Ti_{0.43}Zr_{0.37}O_3$ and 10.0% by weight of NiO.

The piezoelectric element was measured for flexural displacement, which was larger than that of the piezoelectric element of Example 4, at 2.29 μm. Further, the dispersion state of NiO in piezoelectric was examined by an EPMA analysis, which indicated that NiO was dispersed in the piezoelectric in such a concentration gradient that the NiO concentration became higher from the interface between electrode and piezoelectric towards the thickness direction of the piezoelectric. The results are shown in Table 4.

TABLE 4

| | Concentration gradient of NiO | Flexural displacement (μm) |
|---|---|---|
| Example 4 | Uniform | 2.11 |
| Example 5 | Surface concentration was high. | 2.29 |

EXAMPLE 6 AND COMPARATIVE EXAMPLES 5 and 6

Piezoelectric elements were produced in the same manner as in Example 1 except that there were used piezoelectric materials having compositions shown in Table 5.

The piezoelectric elements were measured for flexural displacement. In the piezoelectric element of Example 6 wherein the content of Mg relative to Nb in piezoelectric material was in the range of the present invention (y=0.97), the flexural displacement was large at 2.03 μm.

In contrast, in the piezoelectric element of Comparative Example 5 wherein the content of Mg relative to Nb in piezoelectric material was small (y=0.85), the flexural displacement was small at 1.21 μm; and in the piezoelectric element of Comparative Example 6 wherein the content of Mg relative to Nb in piezoelectric material was large (y=1.15), the flexural displacement was also small at 1.55 μm. The results are shown in Table 5.

TABLE 5

| | Formulation of $PbMg_{1/3}Nb_{2/3}O_3$—$PbZrO_3$—$PbTiO_3$ ternary system solid solution composition | | | | | | | NiO | Flexural |
|---|---|---|---|---|---|---|---|---|---|
| | Pb-replacing element | | | | | | | Content | displacement |
| | Kind of element | Proportion (mole %) | x | Y | a | b | c | (wt. %) | (μm) |
| Example 6 | Ba | 4.0 | 1.00 | 0.97 | 0.370 | 0.380 | 0.250 | 2.0 | 2.03 |
| | La | 0.8 | | | | | | | |
| Comparative Example 5 | Ba | 4.0 | 1.00 | 0.85 | 0.370 | 0.380 | 0.250 | 2.0 | 1.21 |
| | La | 0.8 | | | | | | | |
| Comparative Example 6 | Ba | 4.0 | 1.00 | 1.15 | 0.370 | 0.380 | 0.250 | 2.0 | 1.55 |
| | La | 0.8 | | | | | | | |

EXAMPLE 7 and COMPARATIVE EXAMPLE 7

Piezoelectric elements were produced in the same manner as in Example 1 except that there were used piezoelectric materials having compositions shown in Table 6.

The piezoelectric elements were measured for flexural displacement. In the piezoelectric element of Example 7 wherein the content of Pb in piezoelectric material was in the range of the present invention (x=0.98), the flexural displacement was large at 2.23 μm.

In contrast, in the piezoelectric element of Comparative Example 7 wherein the content of Pb in piezoelectric material was small (x=0.93), the flexural displacement was small at 1.75 μm. The results are shown in Table 6.

TABLE 6

| | Formulation of $PbMg_{1/3}Nb_{2/3}O_3$—$PbZrO_3$—$PbTiO_3$ ternary system solid solution composition | | | | | | NiO Content | Flexural displacement |
|---|---|---|---|---|---|---|---|---|
| | Pb-replacing element | x | Y | a | b | c | (wt. %) | (μm) |
| Example 7 | None | 0.98 | 0.97 | 0.375 | 0.375 | 0.250 | 1.5 | 2.23 |
| Comparative Example 7 | None | 0.93 | 0.85 | 0.375 | 0.375 | 0.250 | 1.5 | 1.75 |

EXAMPLES 8 TO 11

Piezoelectric elements were produced in the same manner as in Example 1 except that there were used piezoelectric materials having compositions shown in Table 7.

The piezoelectric elements were measured for flexural displacement. In all of the piezoelectric elements of Examples 8 to 11, the flexural displacements were relatively large at 1.89 to 2.16 μm.

In the piezoelectric element of Example 9 using an piezoelectric material made of a composition wherein 5.0 mole % of Pb was replaced by Sr and the piezoelectric element of Example 10 made of a composition wherein 10.0 mole % of Pb was replaced by Ba, the flexural displacements were 2.16 μm and 2.10 μm, respectively, and were larger than that (2.02 μm) of the piezoelectric element of Example 8 using a piezoelectric material made of a composition wherein no replacement of Pb was made.

In contrast, in the piezoelectric element of Example 11 using an piezoelectric material made of a composition wherein 7.5 mole % of Pb was replaced by Sr and 7.5 mole % of Pb was replaced by Ca (total 15 mole % of Pb was replaced), the flexural displacement was 1.89 μm and smaller than that (2.02 μm) of the piezoelectric element of Example 8 using a piezoelectric material made of a composition wherein no replacement of Pb was made. The results are shown in Table 7.

TABLE 7

Formulation of $PbMg_{1/3}Nb_{2/3}O_3$—$PbZrO_3$—$PbTiO_3$ ternary system solid solution composition

| | Pb-replacing element | | | | | | | NiO | Flexural |
| | Kind of element | Proportion (mole %) | x | Y | a | b | c | Content (wt. %) | displacement (μm) |
| --- | --- | --- | --- | --- | --- | --- | --- | --- | --- |
| Example 8 | None | — | 1.00 | 0.97 | 0.375 | 0.375 | 0.250 | 1.0 | 2.02 |
| Example 9 | Sr | 5.0 | 1.00 | 0.97 | 0.375 | 0.375 | 0.250 | 1.0 | 2.16 |
| Example 10 | Ba | 10.0 | 1.00 | 0.97 | 0.375 | 0.375 | 0.250 | 1.0 | 2.10 |
| Example 11 | Ba Ca | 7.5 7.5 | 1.00 | 0.97 | 0.375 | 0.375 | 0.250 | 1.0 | 1.89 |

EXAMPLES 12 TO 14

Piezoelectric elements were produced in the same manner as in Example 1 except that there were used piezoelectric materials having compositions shown in Table 8.

The piezoelectric elements were measured for flexural displacement. In all of the piezoelectric elements of Examples 12 to 14, the flexural displacements were relatively large at 1.78 to 2.20 μm.

In the piezoelectric element of Example 13 using an piezoelectric material made of a composition wherein 0.8 mole % of Pb was replaced by La, the flexural displacement was 2.20 μm and was larger than that (2.02 μm) of the piezoelectric element of Example 12 using a piezoelectric material made of a composition wherein no replacement of Pb was made.

In contrast, in the piezoelectric element of Example 14 using an piezoelectric material made of a composition wherein 1.5 mole % of Pb was replaced by La, the flexural displacement was 1.78 μm and was smaller than that (2.02 μm) of the piezoelectric element of Example 12. The results are shown in Table 8.

TABLE 8

Formulation of $PbMg_{1/3}Nb_{2/3}O_3$—$PbZrO_3$—$PbTiO_3$ ternary system solid solution composition

| | Pb-replacing element | | | | | | | NiO | Flexural |
| | Kind of element | Proportion (mole %) | x | Y | a | b | c | Content (wt. %) | displacement (μm) |
| --- | --- | --- | --- | --- | --- | --- | --- | --- | --- |
| Example 12 | None | — | 1.00 | 0.97 | 0.375 | 0.375 | 0.250 | 1.0 | 2.02 |
| Example 13 | La | 0.8 | 1.00 | 0.97 | 0.375 | 0.375 | 0.250 | 1.0 | 2.20 |
| Example 14 | La | 1.5 | 1.00 | 0.97 | 0.375 | 0.375 | 0.250 | 1.0 | 1.78 |

EXAMPLES 15 AND 16 AND COMPARATIVE EXAMPLE 8

Piezoelectric elements were produced in the same manner as in Example 1 except that there were used a piezoelectric material containing 98.5% by weight of $Pb_{1.00}(Mg_{1/3}Nb_{2/3})_{0.20}Ti_{0.43}Zr_{0.37}O_3$ and 1.5% by weight of NiO and atmosphere-controlling materials having formulations shown in Table 9.

The piezoelectric elements were measured for flexural displacement. In the piezoelectric element of Example 15 produced in the co-presence of an atmosphere-controlling material having the same formulation as the ceramic composition constituting the piezoelectric, the flexural displacement was large at 2.20 μm; and in the piezoelectric element of Example 16 produced in the co-presence of an atmosphere-controlling material having a formulation of higher NiO content than that of the ceramic composition constituting the piezoelectric, the flexural displacement was even larger at 2.42 μm.

In contrast, in the piezoelectric element of Comparative Example 8 produced in the co-presence of an atmosphere-controlling material having a formulation of lower NiO content than that of the ceramic composition constituting the piezoelectric, the flexural displacement was 2.03 μm and was smaller than those of the piezoelectric elements of Examples 15 and 16. The results are shown in Table 9.

TABLE 9

| | Formulation of PbMg$_{1/3}$Nb$_{2/3}$O$_3$—PbZrO$_3$—PbTiO$_3$ ternary system solid solution composition | | | | | NiO Content (wt. %) | Flexural displacement ($\mu$m) |
|---|---|---|---|---|---|---|---|
| | Pb-replacing element | x | Y | a | b | c | | |
| Example 15 | None | 1.0 | 1.0 | 0.200 | 0.430 | 0.370 | 1.5 | 2.20 |
| Example 16 | None | 1.0 | 1.0 | 0.200 | 0.430 | 0.370 | 8.0 | 2.42 |
| Comparative Example 8 | None | 1.0 | 1.0 | 0.200 | 0.430 | 0.370 | 0.03 | 2.03 |

As described above, the present invention can provide a piezoelectric element which has very high piezoelectric properties, which is superior in vibration transmittability between ceramic substrate and piezoelectric, and which can provide an actuator, sensor, etc., all of small size and high integration; and a process for producing such a piezoelectric element.

What is claimed is:

1. A process for producing a piezoelectric element, which comprises:

coating, on a ceramic substrate or on an electrode(s) formed on a ceramic substrate, a piezoelectric material made of a ceramic composition composed mainly of a PbMg$_{1/3}$Nb$_{2/3}$O$_3$—PbZrO$_3$—PbTiO$_3$ ternary system solid solution composition represented by the following general formula (1) and containing 0.05 to 10.0% by weight, based on the ceramic composition, of NiO, and heat-treating the coated piezoelectric material in the co-presence of an atmosphere-controlling material having a formulation of the same NiO content as the ceramic composition or a formulation of higher Ni content than the ceramic composition, $$Pb_x(Mg_{y/3}Nb_{2/3})_aTi_bZr_cO_3 \tag{1}$$

wherein $0.95 \leq x \leq 1.05$; $0.8 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100, 0.475, 0.425) and (0.375, 0.425, 0.200), and a+b+c=1.000.

2. A process for producing a piezoelectric element, which comprises:

preparing a plurality of different piezoelectric materials each made of a ceramic composition composed mainly of a PbMg$_{1/3}$Nb$_{2/3}$O$_3$—PbZrO$_3$—PbTiO$_3$ ternary system solid solution composition represented by the following general formula (1) and having a different NiO content, coating these piezoelectric materials in order of the low NiO content piezoelectric materials on a ceramic substrate or on an electrode(s) formed on a ceramic substrate, and heat-treating the coated piezoelectric materials, $$Pb_x(Mg_{y/3}Nb_{2/3})_aTi_bZr_cO_3 \tag{1}$$

wherein $0.95 \leq x \leq 1.05$; $0.8 \leq y \leq 1.0$; a, b and c are decimals falling in a range surrounded by (a,b,c)=(0.550, 0.425, 0.025), (0.550, 0.325, 0.125), (0.375, 0.325, 0.300), (0.100, 0.425, 0.475), (0.100, 0.475, 0.425) and (0.375, 0.425, 0.200), and a+b+c=1.000.

* * * * *